US00PP29059P3

(12) United States Plant Patent
van den Hoogen

(10) Patent No.: US PP29,059 P3
(45) Date of Patent: Mar. 6, 2018

(54) ***VERONICA* PLANT NAMED 'ALLV1461'**

(50) Latin Name: ***Veronica longifolia*×*Veronica spicata***
Varietal Denomination: Allv1461

(71) Applicant: Wilhelmus T. J. van den Hoogen, Cuijk (NL)

(72) Inventor: Wilhelmus T. J. van den Hoogen, Cuijk (NL)

(73) Assignee: Allplants Holding B.V., Cuijk (NL)

( * ) Notice: Subject to any disclaimer, the term of this patent is extended or adjusted under 35 U.S.C. 154(b) by 40 days.

(21) Appl. No.: 14/998,861

(22) Filed: Feb. 23, 2016

(65) Prior Publication Data

US 2017/0245410 P1 Aug. 24, 2017

(51) Int. Cl.
*A01H 5/02* (2006.01)

(52) U.S. Cl.
USPC ..... Plt./251

(58) Field of Classification Search
USPC ..... Plt./251
See application file for complete search history.

(56) References Cited

PUBLICATIONS

UPOV—International Union for the Protection of New Varieties of Plants; PLUTO: Plant Variety Database, updated on May 12, 2017, citation for 'ALLV1461' (1 page).*

* cited by examiner

*Primary Examiner* — Susan McCormick Ewoldt
(74) *Attorney, Agent, or Firm* — C. A. Whealy

(57) ABSTRACT

A new and distinct cultivar of *Veronica* plant named 'Allv1461', characterized by its upright plant habit; freely flowering habit; dense inflorescences with numerous lilac-colored flowers; long flowering period; and suitability as a garden or container plant.

2 Drawing Sheets

Botanical designation: *Veronica longifolia*×*Veronica spicata*.
Cultivar denomination: 'ALLV1461'.

BACKGROUND OF THE INVENTION

The present invention relates to a new and distinct cultivar of *Veronica* plant, botanically known as *Veronica longifolia*× *Veronica spicata* and hereinafter referred to by the name 'Allv1461'.

The new *Veronica* plant is a product of a planned breeding program conducted by the Inventor in Cuijk, The Netherlands. The objective of the breeding program is to create new attractive *Veronica* plants that can be used as a garden or container plant.

The new *Veronica* plant originated from an open-pollination in July, 2013 of a proprietary selection of *Veronica longifolia*×*Veronica spicata* identified as code number 9702, not patented, as the female, or seed, parent with an unknown selection of *Veronica longifolia*×*Veronica spicata* as the male, or pollen, parent. The new *Veronica* plant was discovered and selected by the Inventor as a single flowering plant from within the progeny of the stated open-pollination in a controlled environment in Cuijk, The Netherlands in July, 2014.

Asexual reproduction of the new *Veronica* plant by vegetative cuttings in a controlled environment in Cuijk, The Netherlands, since March, 2015 has shown that the unique features of this new *Veronica* plant are stable and reproduced true to type in successive generations.

SUMMARY OF THE INVENTION

Plants of the new *Veronica* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Allv1461'. These characteristics in combination distinguish 'Allv1461' as a new and distinct *Veronica* plant:

1. Upright plant habit.
2. Freely flowering habit.
3. Dense inflorescences with numerous lilac-colored flowers.
4. Long flowering period.
5. Suitable as a garden or container plant.

Plants of the new *Veronica* differ primarily from plants of the female parent selection in the following characteristics:

1. Plants of the new *Veronica* are shorter than plants of the female parent selection.
2. Plants of the new *Veronica* and the female parent selection differ in flower color as plants of the female parent selection have blue-colored flowers.

Plants of the new *Veronica* can be compared to plants of *Veronica longifolia* 'Allbizarre', not patented. In side-by-side comparisons conducted in Cuijk, The Netherlands, plants of the new *Veronica* differ primarily from plants of 'Allbizarre' in the following characteristics:

1. Plants of the new *Veronica* are shorter than plants of 'Allbizarre'.
2. Plants of the new *Veronica* have terminal and axillary inflorescences whereas plants of 'Allbizarre' only have terminal inflorescences.

3. Flowers of plants of the new *Veronica* have stamens whereas flowers of plants of 'Allbizarre' do not develop stamens.

BRIEF DESCRIPTION OF THE PHOTOGRAPHS

The accompanying colored photographs illustrate the overall appearance of the *Veronica* plant showing the colors as true as it is reasonably possible to obtain in colored reproductions of this type. Colors in the photographs may differ slightly from the color values cited in the detailed botanical description which accurately describe the actual colors of the new *Veronica* plant.

The photograph on the first sheet comprises a side perspective view of a typical flowering plant of 'Allv1461'.

The photograph at the top of the second sheet is a close-up view of typical inflorescences of 'Allv1461'.

The photograph at the bottom of the second sheet is a close-up view of the upper surface of typical leaves of 'Allv1461'.

DETAILED BOTANICAL DESCRIPTION

Plants used for the aforementioned photographs and following description were grown during the summer in ground beds in an outdoor nursery in Rijswijk, The Netherlands and under cultural practices typical of commercial *Veronica* production. During the production of the plants, day temperatures ranged from 15° C. to 30° C. and night temperatures ranged from 6° C. to 18° C. Plants were four months old when the photographs and the description were taken. In the following description, color references are made to The Royal Horticultural Society Colour Chart, 2015 Edition, except where general terms of ordinary dictionary significance are used.

Botanical classification: *Veronica longifolia*×*Veronica spicata* 'Allv1461'.

Parentage:

*Female, or seed, parent*.—Proprietary selection of *Veronica longifolia*×*Veronica spicata* identified as code number 9702, not patented.

*Male, or pollen, parent*.—Unknown selection of *Veronica longifolia*×*Veronica spicata*, not patented.

Propagation:

*Type cutting*.—Vegetative cuttings.

*Time to initiate roots, summer*.—About 10 to 14 days at temperatures ranging from 12° C. to 30° C.

*Time to produce a rooted young plant, summer*.—About 24 to 32 days at temperatures ranging from 12° C. to 30° C.

*Root description*.—Fine, fleshy; typically white in color, actual color of the roots is dependent on substrate composition, water quality, fertilizer type and formulation, substrate temperature and physiological age of roots.

*Rooting habit*.—Freely branching; dense.

Plant description:

*Plant type*.—Herbaceous perennial.

*Plant and growth habit*.—Broadly upright inverted triangle; freely basal branching habit with about 47 lateral branches developing per plant; moderately vigorous growth habit.

*Plant height*.—About 49 cm.

*Plant width*.—About 46.2 cm.

*Lateral branch description*.—Length: About 17.4 cm. Diameter: About 3 mm. Internode length: About 3.9 cm. Strength: Strong. Aspect: Main stems, mostly upright; lateral branches, about 30° from main stem. Texture and luster: Densely pubescent; matte. Color: Close to 144B.

Leaf description:

*Arrangement*.—Opposite, simple.

*Length*.—About 7.4 cm.

*Width*.—About 3.1 cm.

*Shape*.—Ovate to narrowly ovate; moderately carinate.

*Apex*.—Acute.

*Base*.—Truncate.

*Margin*.—Serrate.

*Texture and luster, upper surface*.—Glabrous; moderately glossy.

*Texture and luster, lower surface*.—Mostly glabrous and along midvein, sparsely pubescent; matte.

*Venation pattern*.—Pinnate.

*Color*.—Developing leaves, upper surface: Close to 143A. Developing leaves, lower surface: Close to 143B. Fully expanded leaves, upper surface: Darker than between 139A and 147A; venation, close to 147C to 147D. Fully expanded leaves, lower surface: Close to N137D; venation, close to 144B.

*Petioles*.—Length: About 1.2 cm. Diameter: About 2 mm. Texture, upper and lower surfaces: Smooth. Color, upper and lower surfaces: Close to 144B.

Flower description:

*Flower arrangement and shape*.—Single campanulate flowers arranged on dense terminal and axillary racemes; flowers face mostly outwardly.

*Flowering habit*.—Freely flowering habit with about 250 flowers developing per inflorescence and more than 6,000 flowers developing per plant during the flowering season.

*Fragrance*.—Faint; somewhat moldy.

*Natural flowering season*.—Long flowering period; plants flower continuously from mid-June to late September in The Netherlands.

*Flower longevity as a cut flower*.—About ten days; flowers not persistent.

*Flower longevity on the plant*.—About 30 days; flowers not persistent.

*Flower buds*.—Length: About 4.5 mm. Diameter: About 2 mm. Shape: Ovate. Color: Close to 85C; towards the base, close to 85D.

*Inflorescence height*.—About 14.1 cm.

*Inflorescence diameter*.—About 2.2 cm.

*Flower diameter*.—About 7 mm.

*Flower height*.—About 8 mm.

*Petals*.—Quantity and arrangement: Four in a single whorl; petals fused about 33.3% of the length from the base. Length: About 6 mm. Width: About 2 mm to 3 mm. Shape: Obovate. Apex: Obtuse. Margin: Entire. Texture and luster, upper and lower surfaces: Smooth, glabrous; matte. Color: When opening, upper and lower surfaces: Close to between 85D and 91C. Fully opened, upper and lower surfaces: Close to 91C to 91D; color becoming closer to 91C with development.

*Sepals*.—Quantity and arrangement: Four in a single whorl; sepals fused about 25% of the length from the base. Length: About 1.5 mm to 2.5 mm. Width: About 1 mm. Shape: Narrowly ovate. Apex: Acute. Margin: Entire. Texture, upper and lower surfaces: Smooth, glabrous. Color: When opening and fully opened, upper surface: Close to 143B. When opening and fully opened, lower surface: Close to 143B.

*Peduncles*.—Length: About 13.6 cm. Diameter: About 2.5 mm. Aspect: Mostly upright. Strength: Strong. Texture: Smooth, glabrous. Color: Close to 145A to 145B.

*Pedicels*.—Length: About 1 mm. Diameter: About 0.75 mm. Aspect: About 45° from peduncle axis. Strength: Strong. Texture: Smooth, glabrous. Color: Close to 144B to 144C.

*Reproductive organs*.—Stamens: Quantity per flower: Two. Filament length: About 4.5 mm. Filament color: Close to 91D to lighter than 91D. Anther shape: Double reniform, narrow. Anther length: About 2 mm. Anther color: Close to 195C. Pollen amount: Moderate. Pollen color: Close to 8D. Pistils: Quantity per flower: One. Pistil length: About 5 mm. Stigma shape: Clavate. Stigma color: Close to 93C. Style length: About 4.5 mm. Style color: Close to 91C to 91D. Ovary color: Close to 144D.

*Seeds and fruits*.—Seed and fruit development has not been observed on plants of the new *Veronica* to date.

Disease & pest resistance: Plants of the new *Veronica* have not been noted to be resistant to pathogens and pests common to *Veronica* plants.

Garden performance: Plants of the new *Veronica* have exhibited good garden performance and to be tolerant to rain, wind, high temperatures about 35° C. and to be hardy to USDA Hardiness Zone 4.

It is claimed:

1. A new and distinct *Veronica* plant named 'Allv1461' as illustrated and described.

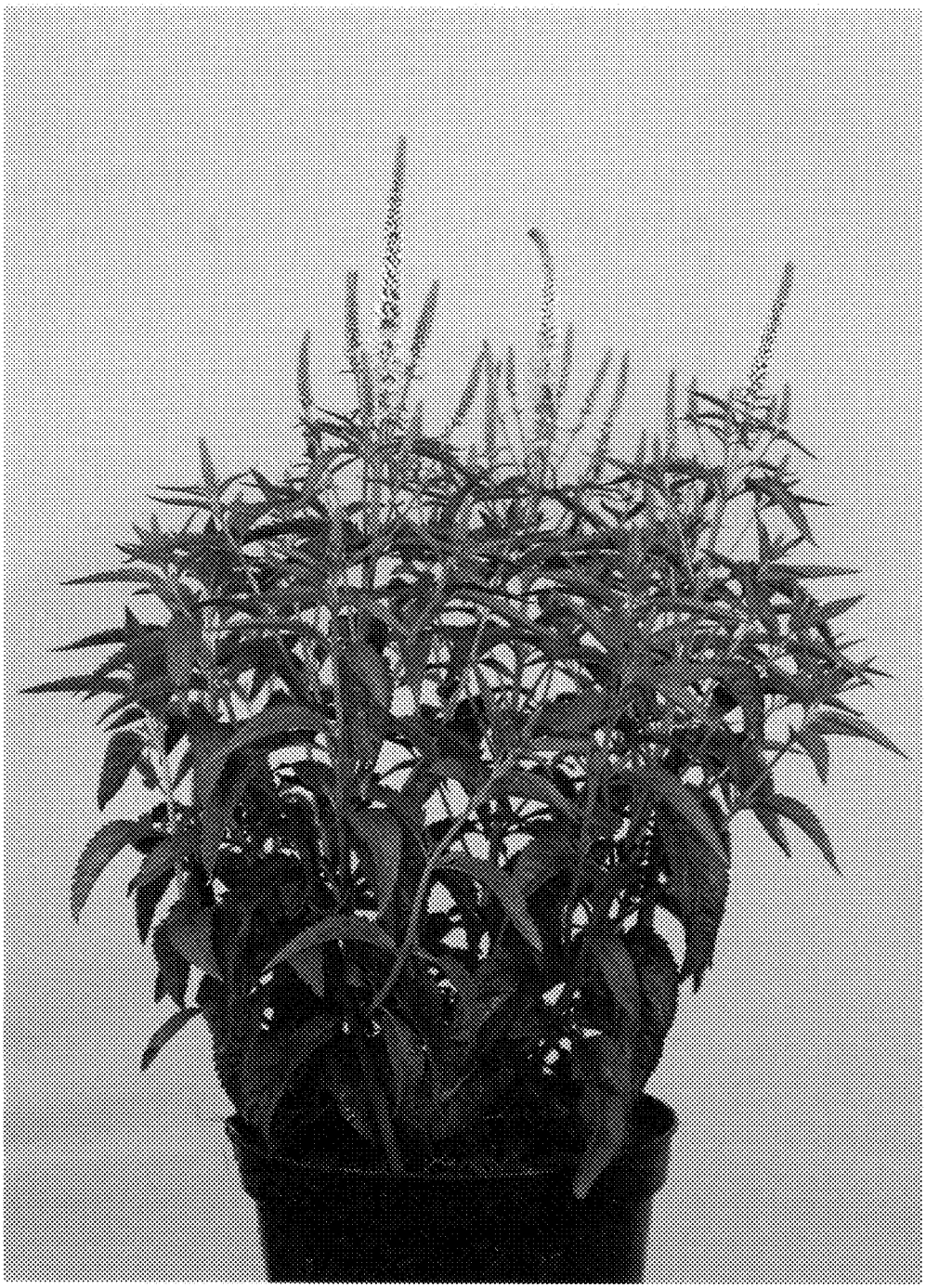

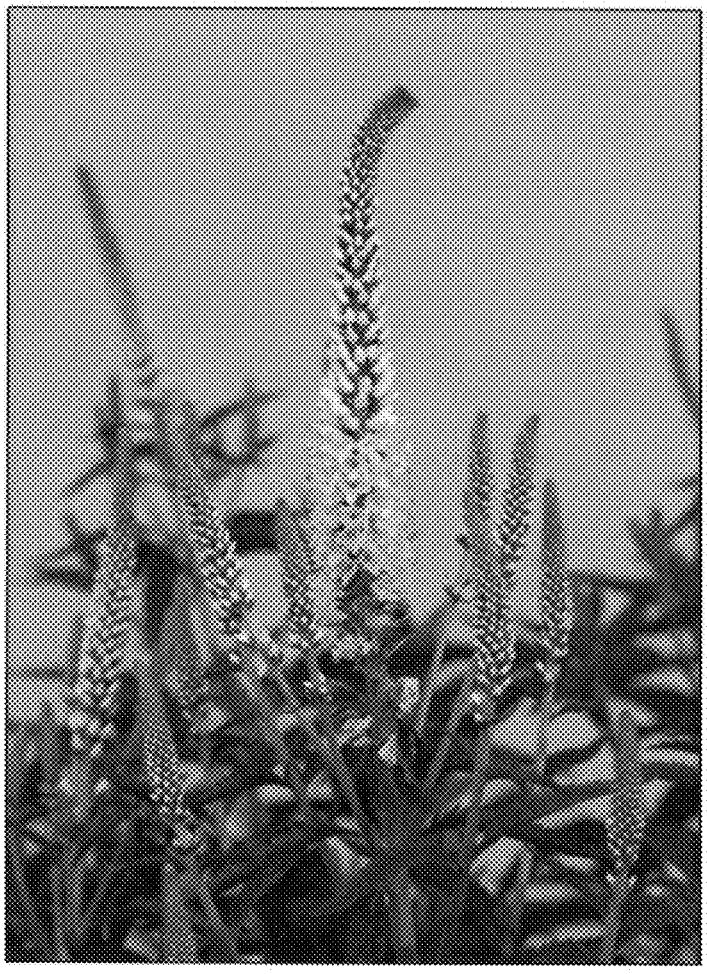
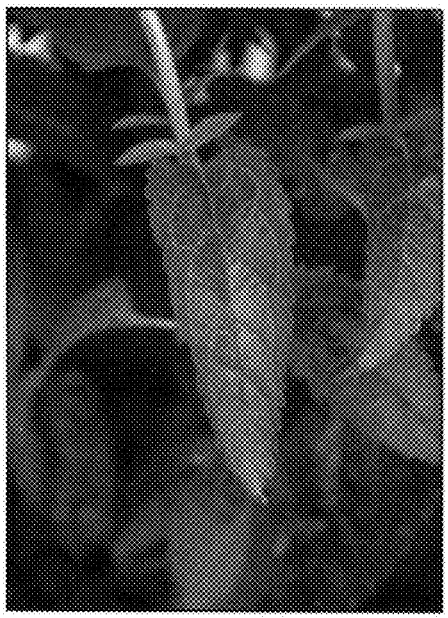

* * * * *